United States Patent [19]
Yabe et al.

[11] Patent Number: 5,695,447
[45] Date of Patent: Dec. 9, 1997

[54] ENDOSCOPE SYSTEM INCLUDING ENDOSCOPE AND DISPOSABLE PROTECTION COVER

[75] Inventors: Hisao Yabe, Hachioji; Yoshihiro Iida, Tama; Akira Suzuki; Hideo Ito, both of Hachioji; Yoshio Tashiro, Hino; Minoru Yamazaki, Hachioji; Osamu Tamada, Hachioji; Hiroki Hibino, Hachioji, all of Japan

[73] Assignee: Olympus Optical Company, Ltd., Osaka, Japan

[21] Appl. No.: 51,100

[22] Filed: Apr. 22, 1993

[30] Foreign Application Priority Data

| Mar. 16, 1993 | [JP] | Japan | 5-011593 U |
| Mar. 16, 1993 | [JP] | Japan | 5-011595 U |
| Mar. 16, 1993 | [JP] | Japan | 5-055861 |

[51] Int. Cl.$^6$ .................................... A61B 1/04
[52] U.S. Cl. .................... 600/121; 600/123; 600/125; 600/127; 600/153
[58] Field of Search .............. 128/4, 6; 600/121, 600/122, 123, 124, 125, 129, 153, 156, 146, 142

[56] References Cited

U.S. PATENT DOCUMENTS

| 3,035,691 | 5/1962 | Rasmussen et al. |
| 3,633,758 | 1/1972 | Morse. |
| 4,108,211 | 8/1978 | Tanaka .................. 600/142 X |
| 4,216,767 | 8/1980 | Aoshiro. |
| 4,288,882 | 9/1981 | Takeuchi. |
| 4,366,901 | 1/1983 | Short. |
| 4,404,963 | 9/1983 | Kohri. |
| 4,646,722 | 3/1987 | Silverstein et al. |
| 4,715,360 | 12/1987 | Akui et al. |
| 4,721,097 | 1/1988 | D'Amelio. |
| 4,741,326 | 5/1988 | Sidall et al. |
| 4,779,727 | 10/1988 | Taterka et al. |
| 4,825,850 | 5/1989 | Opie et al. |
| 4,858,001 | 8/1989 | Milbank et al. |
| 4,869,238 | 9/1989 | Opie et al. |
| 4,877,033 | 10/1989 | Seitz. |
| 4,878,485 | 11/1989 | Adair. |
| 4,907,395 | 3/1990 | Opie et al. |
| 4,947,827 | 8/1990 | Opie et al. |
| 4,991,564 | 2/1991 | Takahashi et al. |
| 4,991,565 | 2/1991 | Takahashi et al. |
| 5,025,778 | 6/1991 | Silverstein et al. |
| 5,042,112 | 8/1991 | Dunklee. |
| 5,050,585 | 9/1991 | Takahashi. |
| 5,105,942 | 4/1992 | van Veen et al. |
| 5,131,537 | 7/1992 | Gonzales. |
| 5,198,894 | 3/1993 | Hicks. |

(List continued on next page.)

FOREIGN PATENT DOCUMENTS

| 0341719A1 | 11/1989 | European Pat. Off. |
| 0349479A1 | 1/1990 | European Pat. Off. |
| 2805298A1 | 8/1978 | Germany. |
| 376128B2 | 10/1989 | Japan. |
| 3264037A | 11/1991 | Japan. |
| 4325138 | 11/1992 | Japan. |

*Primary Examiner*—Beverly M. Flanagan
*Attorney, Agent, or Firm*—Watson Cole Stevens Davis, P.L.L.C.

[57] ABSTRACT

In an endoscope system including an endoscope having an insertion section to be inserted into a cavity under inspection, a bending portion which is provided in the insertion section near a distal end thereof and is bent in at least up and down directions and an operation section to which a proximal end of the insertion section is connected and a disposable protection cover having an insertion section dover for covering the insertion section of the endoscope and having formed therein an insertion section inserting channel into which the insertion section of the endoscope is insertable and conduit channels, the insertion section inserting channel and conduit channels are both crossed by a line which is parallel with the up and down directions, so that the distal end of the insertion section can be correctly bent in the up and down directions without being influenced by the conduit channels.

9 Claims, 12 Drawing Sheets

U.S. PATENT DOCUMENTS

| | | |
|---|---|---|
| 5,201,908 | 4/1993 | Jones . |
| 5,217,001 | 6/1993 | Nakao et al. . |
| 5,237,984 | 8/1993 | Williams, III et al. . |
| 5,257,617 | 11/1993 | Takahashi ............................. 128/4 |
| 5,301,657 | 4/1994 | Lafferty et al. . |
| 5,334,142 | 8/1994 | Paradis . |
| 5,363,843 | 11/1994 | Daneshvar . |
| 5,419,311 | 5/1995 | Yabe et al. . |

FIG_1

FIG_6
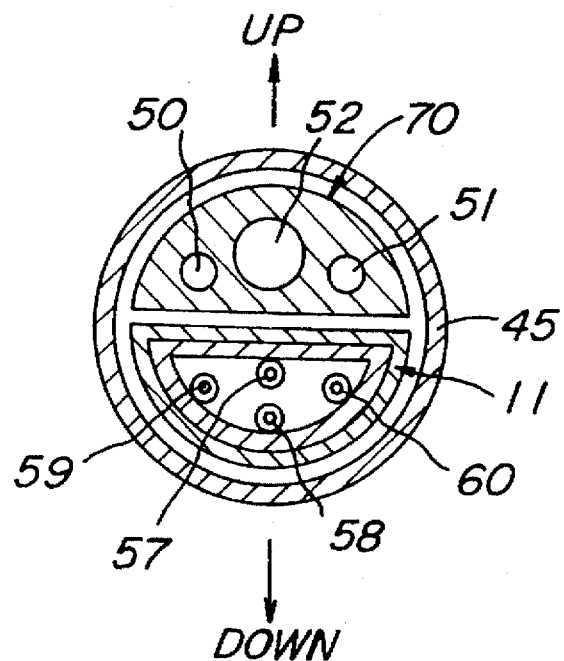
FIG_7
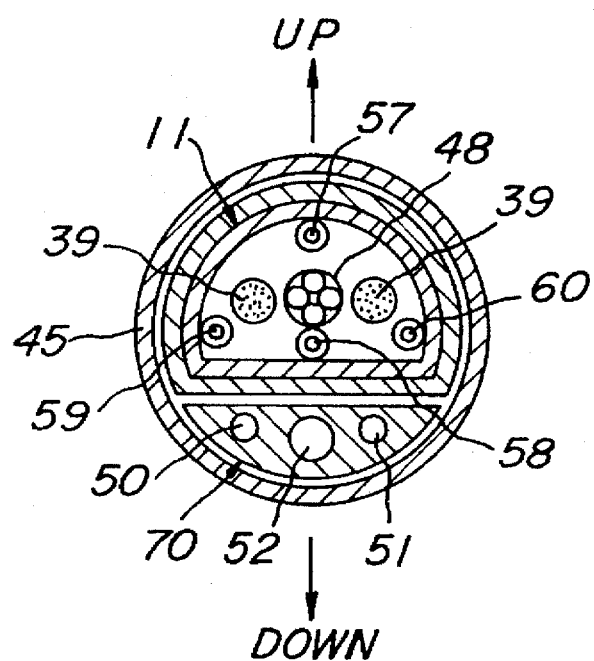

FIG_8
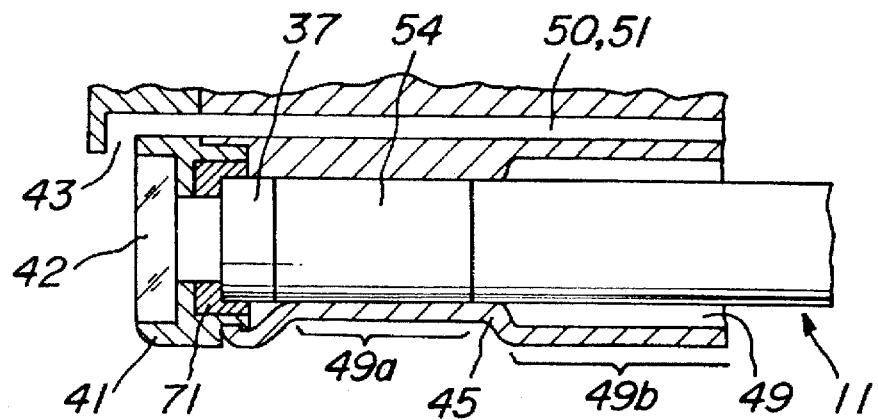
FIG_9
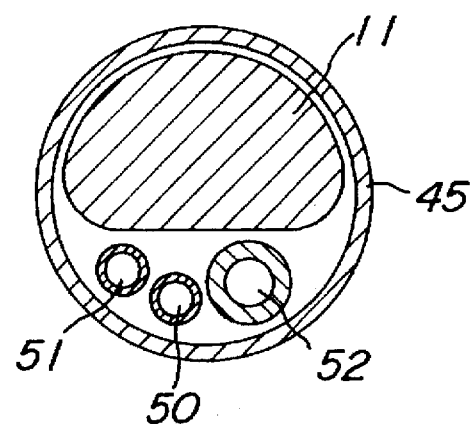
FIG_10
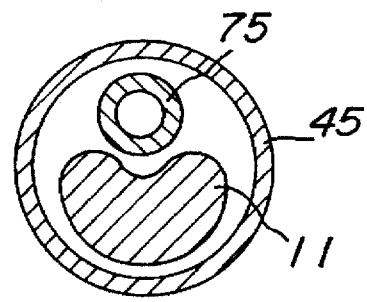

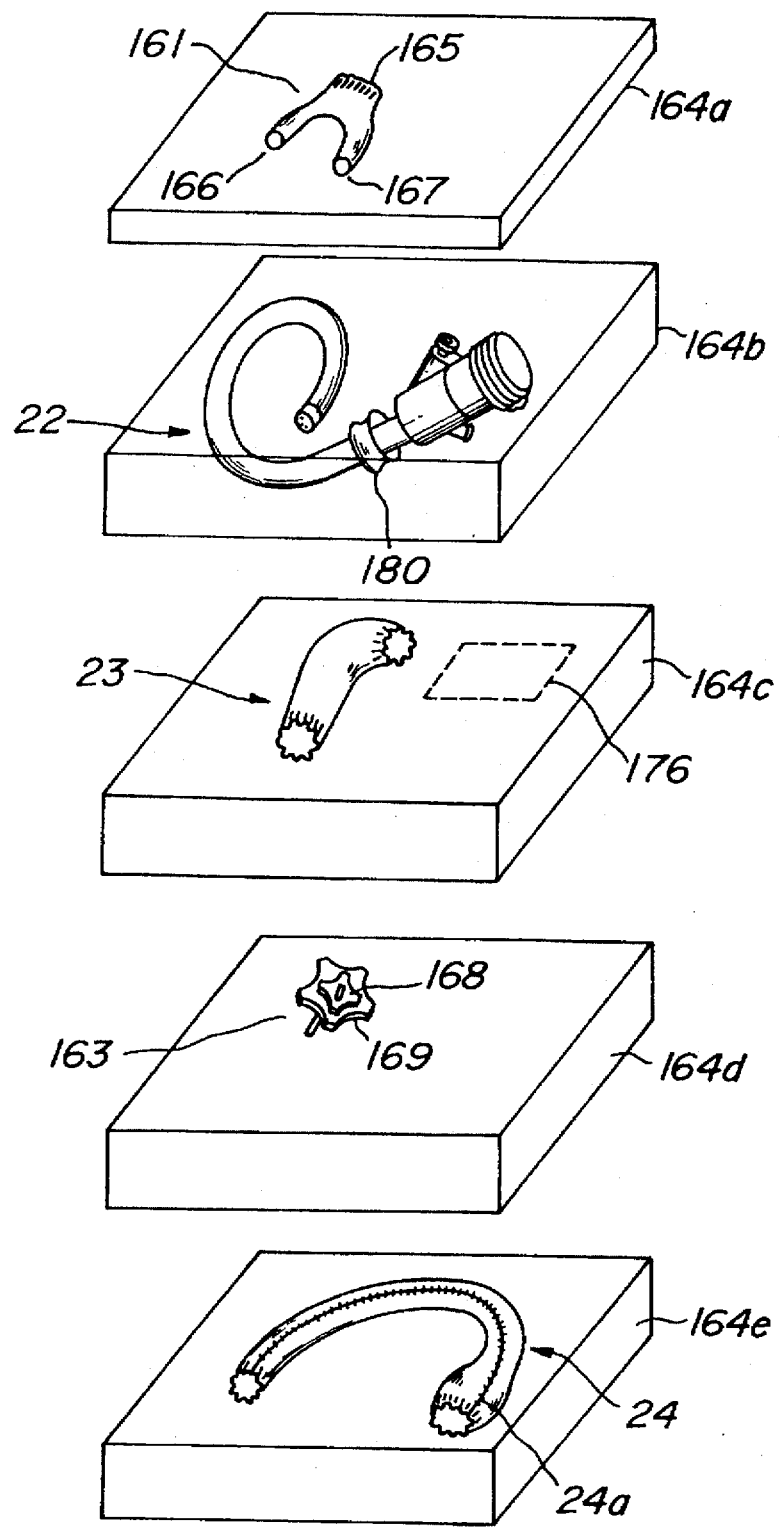
FIG_11

FIG_12
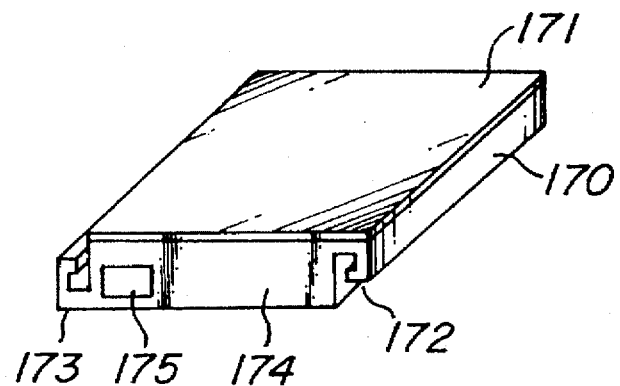
FIG_13
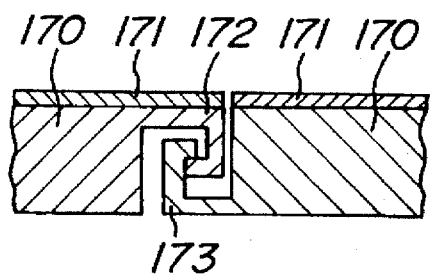
FIG_14
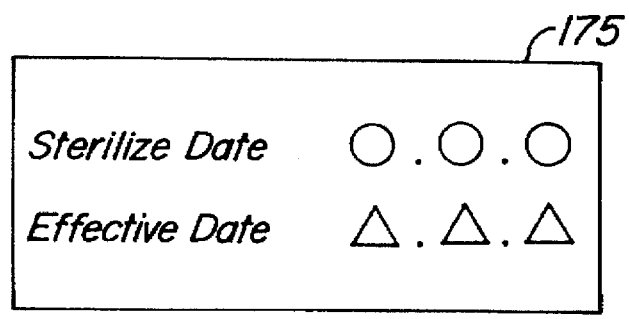

FIG._16
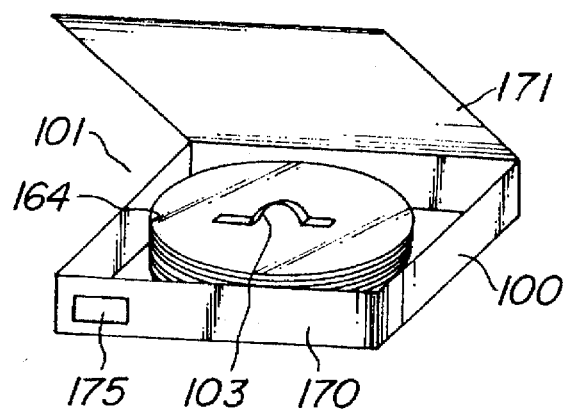
FIG._17
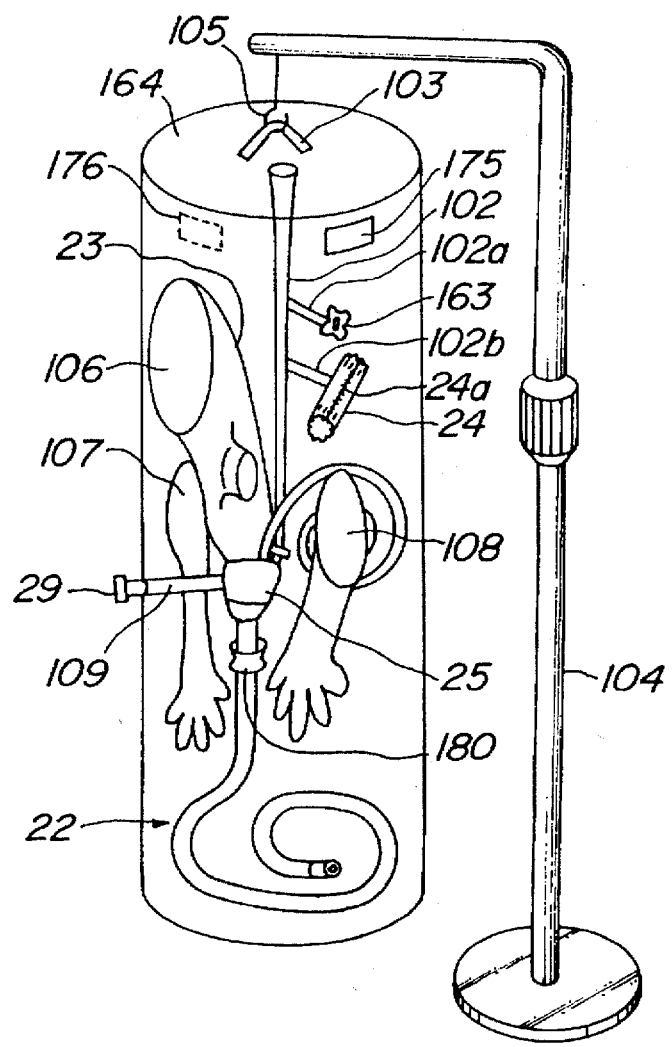

FIG_18
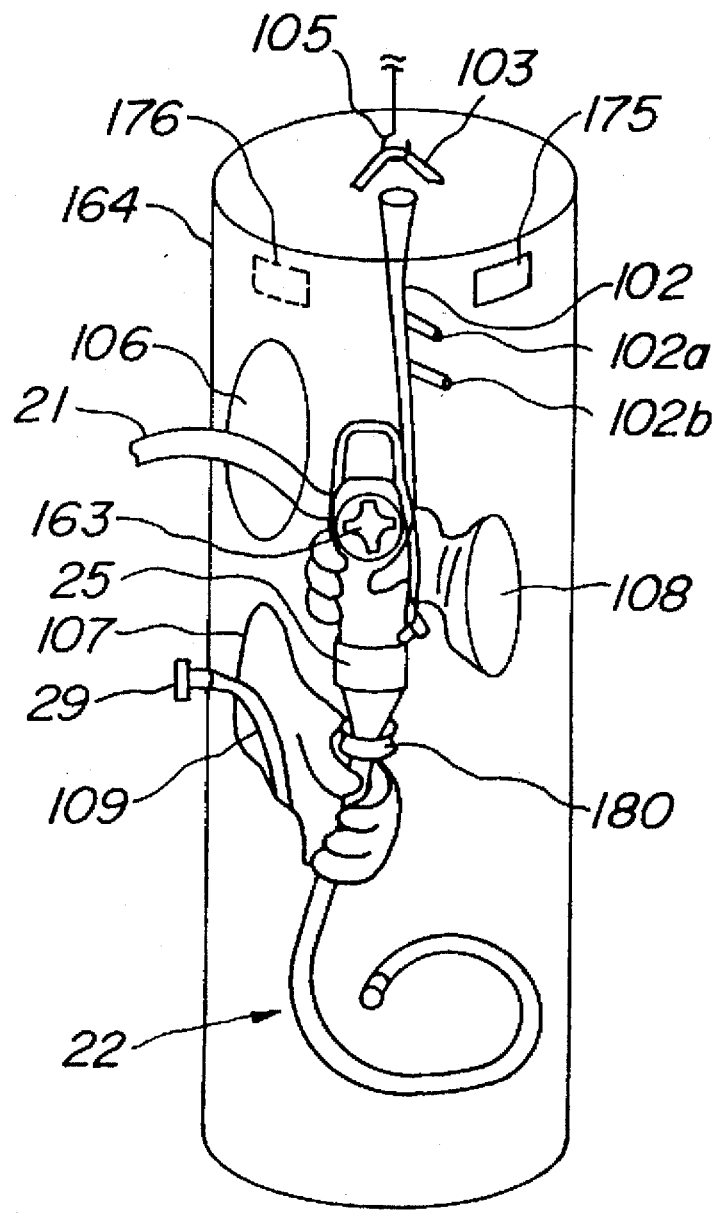

FIG._19
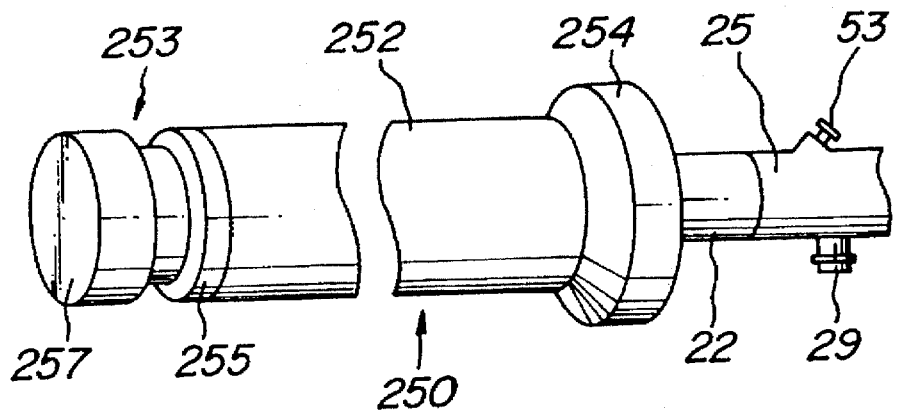
FIG._20
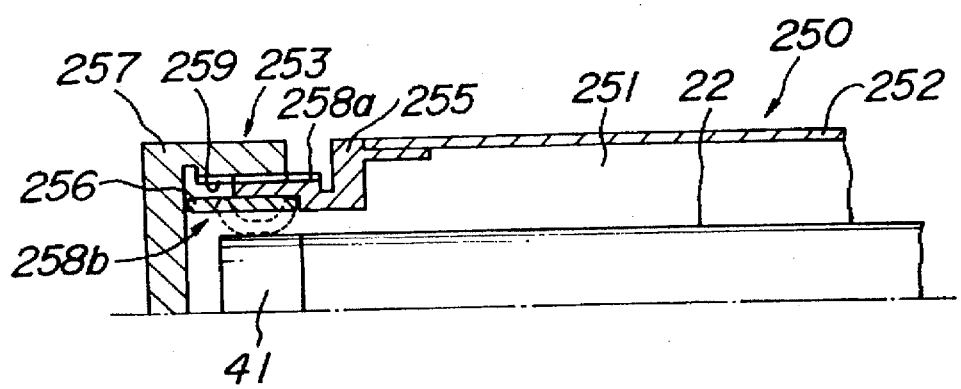
FIG._21
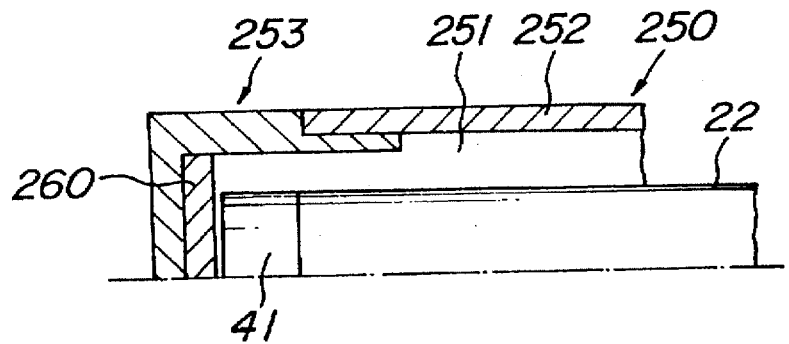

ENDOSCOPE SYSTEM INCLUDING ENDOSCOPE AND DISPOSABLE PROTECTION COVER

BACKGROUND OF THE INVENTION

1. Field of the Invention

The present invention relates to an endoscope system including an endoscope and a disposable protection cover for covering the endoscope, and also relates to a disposable protection cover and an endoscope for use in such an endoscope system.

2. Description of the Related Art

An endoscope system has been widely utilized for providing diagnostic and therapeutic indications for coeliac cavities of patients and for internal inspection of mechanical structures. To this end, various kinds of endoscopes have been developed. For instance, in order to inspect or treating the oesophagus, stomach and duodenum, upper endoscopes have been utilized. Further, colonoscopes have been developed to examine colons and sigmoidoscopes have been proposed to inspect rectums and sigmoid colons. When the endoscope is used, an insertion portion of the endoscope has to be inserted into a cavity of a patient, so that the outer surface of the insertion section of the endoscope is contaminated with living tissues and liquids. When the thus contaminated endoscope is successively used for another patient, there might be a possibility of infection. Therefore, once the endoscope is used to diagnose and/or treat a patient, it is necessary to clean and sterilize the endoscope. Of course, the cleaning of the endoscope requires a substantial amount of time and during this cleaning time the endoscope cannot be used to perform the endoscopic procedures. In order to mitigate such an idle time, it is necessary to prepare a large number of endoscopes. However, the endoscopes are rather expensive, so that it is practically difficult to prepare a large number of endoscopes, particularly in a small hospital or clinic. Therefore, in almost all hospitals and clinics, in practice, after the endoscope has been used for examining or treating a patient, the endoscope is immediately cleaned. Typically, this cleaning requires several minutes to ten minutes. In order to effect complete washing and sterilization, the cleaning has be to performed for several tens of minutes.

Further, the endoscope has various channels such as an air channel, a water channel, a suction channel, and a forceps channel which extend along the insertion section from a proximal end to a distal end thereof, and these channels, except the forceps channel, are connected via tubes to respective devices such as an air supply pump, a water supply pump, a water suction pump and an air suction pump. These channels are subjected to contact with living tissues and liquids. However, in order to clean these channels of the endoscope completely, a relatively long period of time is required. Thus, the endoscope can not be utilized efficiently during the long cleaning time. In a large hospital or clinics, a large number of endoscopes may be prepared in order to mitigate the problem of cleaning time. However, this solution results in an increase in the operating cost. Further, in small clinics, it is practically impossible to prepare a number of expensive endoscopes.

Moreover, the endoscope might be broken during cleaning and the usable life of the endoscope is liable to be shortened by the cleaning, In order to avoid the above explained various problems, there has been proposed an endoscope system, in which the endoscope is covered with a disposable protection sheath-like cover having channels formed therein. For instance, U.S. Pat. Nos. 4,721,097, 4,741,3126, 4,825,850, 4,869,238, 4,991,564, 4,991,565, 5,050,585 disclose various kinds of disposable protection sheath-like covers having channels formed therein. In U.S. Pat. No. 4,646,722, there is shown an endoscope system in which the endoscope is covered with a protection sheath, while a tube having channels formed therein is inserted into a U-shaped outout formed in an outer surface of the endoscope along a longitudinal axis thereof. Upon diagnosis, the insertion section of the endoscope is covered with the projection sheath and after the inspection, the sheath is removed from the insertion section and is then discarded. Wherefore, it is no longer necessary to clean the endoscope after every the inspection.

In the above mentioned U.S. Patent Specifications, the protection sheath-like cover is constructed to cover only the insertion section of the endoscope, but does not cover an operation section of the endoscope. It should be noted that the operation section of the endoscope is handled by doctors and operators and thus is brought into contact with the living tissues and liquids of a patient. Therefore, in order to remove the contamination of the operation section of the endoscope due to such living tissues and liquids, it is advantageous to cover not only the insertion section, but also the operation section of the endoscope. In European Patent Publication No. 0 349 479 A1, there is disclosed an endoscope system, in which not only the insertion section, but also the operation section of the endoscope are covered with a disposable protection cover. That is to say, the protection cover comprises a sheath-like portion for covering the insertion section of the endoscope and a bag-like portion for covering the operation section, said sheath-like portion and bag-like portion being integrally formed. It has been also proposed to form the sheath-like portion and bag-like portion as separate covers. For instance, in European Patent Publication No. 0 341 719 A1, there is proposed another known endoscope system, in which an insertion section of an endoscope is covered with a disposable protection sheath-like cover and an operation section of the endoscope is covered with a disposable protection bag-like cover which is mated or joined with the protection sheath-like cover in order to prevent the contamination through the junction of the sheath-like cover and the bag-like cover.

In order to treat a cavity of a patient body, it has been proposed to arrange a forceps channel within the sheath-like cover into which an endoscope is inserted.

As explained above, in a disposable protection cover there are formed a forceps channel, an air supply a conduit channel and a water supply conduit channel. These channels are extended within the protection cover. In a lateral cross section of the protection cover, these channels are arranged in a substantially semicircular space and the endoscope having a substantially semicircular cross section is inserted into the remaining substantially semicircular space. It has been further proposed to construct the above mentioned channels in the form of a multi-lumen. It should be noted that the distal end of the insertion section of the endoscope is bent in up and down directions as well as in right and left directions by operating one or two angle knobs provided on the operation section of the endoscope. In practice, the bending in the up and down directions is more important than the bending in the right and left directions. For sake of simplicity, in the present specification, the bending in the up and down directions is called up/down or vertical movement and the bending in the right and left directions is called right/left or horizontal movement. It should be noted that during the actual examination, a posture of the distal end portion of the endoscope is changed at will so that the above-mentioned vertical and horizontal movements do not correspond to the actual vertical and horizontal directions. As explained above, in the practical usage of the endoscope, the vertical movement is frequently effected, but the horizontal movement is performed auxiliarily. Therefore, it is necessary to construct the bending portion of the insertion section to be accurately bendable in the up and direction without tilting in the right and left directions. However, in the known endoscope systems, the direction of the vertical movement of the endoscope with respect to the disposable protection cover has not been carefully considered. Therefore, the conduit channels might prevent correct up and down movement of bending portion of the insertion section. When an endoscope having a circular cross sectional insertion section is used, the up and down directions may be selected at will with respect to the conduit channels, so that the above mentioned problem becomes manifest. The distal end portion of the endoscope having the semicircular cross section is easily bent in a direction perpendicular to a diametric direction of the endoscope, but can not be bent easily in the diametric direction. Therefore, when the protection cover is constructed such that the direction of the up/down movement is set to the diametric direction of the endoscope, the vertical movement of the endoscope can not be performed accurately and a desired portion of the cavity under inspection could not be examined efficiently.

In the known endoscope system, the distal end of the insertion section cover is formed by a rigid member and the insertion section of the endoscope is inserted therein such that its front end is urged against the rigid member. Thus, there is a fear that the front end of the insertion section of the endoscope might be damaged or injured by the contact with the rigid member of the protection cover.

Further in the known endoscope systems, the insertion section inserting channel is formed in the disposable protection cover such that the insertion section is brought into contact with the inner wall of the insertion section inserting channel substantially over its entire length. Such a construction has been adopted in order to bend the distal end portion of the insertion section accurately. That is to say, if the insertion section is loosely inserted into the insertion section inserting channel, the distal end portions of the insertion section and insertion section cover can not be bent accurately when the angle knob provided on the operation section of the endoscope is operated. However, when the insertion section of the endoscope is brought into contact with the inner wall of the insertion section channel formed in the protection cover, the insertion section can not be easily inserted into the channel.

As explained above, the disposable protection cover comprises a plurality of parts such as the insertion section cover, operation section cover and universal cord cover. In the known endoscope system, these parts are installed in separate packages, no that when the endoscope system is used, the necessary cover parts must be taken out of respective packages, and this is very cumbersome. Further, these cover parts have to be used in a correct order in order to attain the efficient operation. However, in practice, these cover parts are not used in the correct order so that a long time is required which might lead to contamination. In this manner, the efficiency of the examination with the aid of the endoscope system including the protection cover might be decreased.

When the endoscope is covered with the disposable protection cover, the protection cover might be contaminated, because this operation is performed in a space in which there are a large number of contamination sources. For instance, when the protection cover is taken out of the package, if the protection cover is brought into contact with a contamination source, the protection cover is contaminated.

After the endoscopic examination, the insertion section of the endoscope is removed from the insertion section cover. In order to carry out this operation safely, it has been proposed to use a discarding cover. After the examination, the insertion section cover in which the insertion section of the endoscope has been inserted is inserted into the discarding cover. In the known endoscope system using the discarding cover, there is not provided a means for coupling the insertion section cover with the discarding cover. Therefore when the insertion section is pulled out of the insertion section cover, the insertion section cover might move relative to the discarding cover, and thus the insertion section can not be removed from the insertion section cover easily.

SUMMARY OF THE INVENTION

The present invention has for its object to provide a novel and useful endoscope system including an endoscope having an insertion section to be inserted into a cavity under inspection and an operation section to which a proximal end of the insertion section is connected, and a disposable protection cover for covering at least the insertion section of the endoscope and having at least one channel formed therein, in which the distal end portion of the insertion section of the endoscope can be bent accurately in the up and down directions.

It is another object of the invention to provide a novel and useful endoscope system, in which only the distal end portion of the insertion section of the endoscope is brought into contact with the protection cover while substantially all the remaining portion of the endoscope are not brought into contact with the inner wall of an insertion section cover so that the insertion section can be easily inserted into the protection cover.

It is another object of the invention to provide a novel and useful endoscope system including an endoscope having an insertion section to be inserted into a cavity under inspection and an operation section to which a proximal end of the insertion section is connected, and a disposable protection cover having an insertion section cover for covering the insertion section of the endoscope, in which the front end of the distal end portion of the insertion section can be effectively protected from the damage or injure.

It is another object of the invention to provide a novel and useful disposable protection cover for use in an endoscope system including an endoscope having an insertion section to be inserted into a cavity under inspection and an operation section to which a proximal end of the insertion section is connected, and a disposable protection cover having an insertion section cover for covering the insertion section of the endoscope and an operation section cover for covering the operation section, in which the insertion section cover and operation section cover are installed in a package such that these covers can be used in a correct order.

It is another object of the invention to provide a novel and useful disposable protection cover for use in an endoscope system including an endoscope having an insertion section to be inserted into a cavity under inspection and an operation section to which a proximal end of the insertion section is connected, and a disposable protection cover having an insertion section cover for covering the insertion section of the endoscope and an operation section cover for covering the operation section, in which the insertion section cover and operation section cover are installed in a package such that these covers can be provided on or removed from the endoscope within the package, so that the these covers and the user can be effectively protected against the contamination.

It is still another object of the invention to provide a novel and useful disposable protection cover for use in an endoscope system including an endoscope having an insertion section to be inserted into a cavity under inspection and an operation section to which a proximal end of the insertion section is connected, and a disposable protection cover having an insertion section cover for covering the insertion section of the endoscope and an outer cover for covering the insertion section cover, in which the insertion section cover can be fixed in the outer cover, so that the insertion section of the endoscope can be easily removed from the insertion section cover within said outer cover.

According to a first aspect of the invention, an endoscope system including a endoscope having an insertion section to be inserted into a cavity under inspection, a bending portion which is provided in the insertion section near a distal end thereof and is bent in at least up and down directions and an operation section to which a proximal end of the insertion section is connected and a disposable protection cover having an insertion section cover for covering the insertion section of the endoscope and having formed therein an insertion section inserting channel into which the insertion section of the endoscope is insertable and at least one conduit channel, includes an improvement being characterized in that the insertion section inserting channel and at least one conduit channel are arranged to be aligned in a direction which is parallel with said up and down directions.

In the disposable protection cover according to the invention, the conduit channel is arranged above or below the insertion section inserting channel, so that the distal end portion of the insertion section of the endoscope can be bent accurately in the up and down directions without being affected by the conduit channel.

According to a second aspect of the invention, an endoscope system including an endoscope having an insertion section to be inserted into a cavity under inspection, a bending portion which is provided in the insertion section near a distal end thereof and is bent in at least up and down directions and an operation section to which a proximal end of the insertion section is connected and a disposable protection cover having an insertion section cover for covering the insertion section of the endoscope includes an improvement being characterized in that a distal end portion of the insertion section cover is formed such that a distal end portion of the insertion section of the endoscope is firmly clamped into the distal end portion of the insertion section cover, but a remaining portion of the insertion section is substantially separated from an insertion section inserting channel.

In this endoscope system according to the invention, only the distal end portion of the insertion section of the endoscope is brought into contact with the inner wall of the insertion section inserting channel, and therefore the insertion section can be easily inserted into and removed from the insertion section cover. In this ease, a bending portion of the insertion section is provided in the distal end portion, a distal end portion of an assembly of the insertion section and insertion section cover can be effectively bent by bending the bending portion of the insertion section of the endoscope.

According to a third aspect of the present invention, a disposable protection cover for use in an endoscope system including an endoscope having an insertion section to be inserted into a cavity under inspection and an operation section to which a proximal end of the insertion section is connected, and a disposable protection cover having an insertion section cover for covering the insertion section of the endoscope and an operation section cover for covering said operation section of the endoscope includes an improvement being characterized in that the insertion section cover and operation section cover are installed in one or more packages such that an order of providing the insertion section cover and operation section cover on the endoscope is easily perceptible to a user.

In such a disposable protection cover according to the invention, upon using the protection cover, the user can use the insertion section cover and operation section cover in the correct order and thus the operation can be performed easily and correctly.

According to a fourth aspect of the present invention, a disposable protection cover for use in an endoscope system including an endoscope having an insertion section to be inserted into a cavity under inspection and an operation section to which a proximal end of the insertion section is connected, and a disposable protection cover having an insertion section cover for covering the insertion section of the endoscope and en operation section cover for covering the operation section of the endoscope includes an improvement being characterized in that the insertion section cover and operation section cover of the protection cover are arranged in a package such that the insertion section and operation section of the endoscope can be covered with the insertion section cover and operation section cover within the package.

By using the disposable protection cover according to the invention, the endoscope can be covered with the protection cover within the package, so that the protection cover can be effectively prevented from being contaminated during the covering operation.

According to a fifth aspect of the present invention, a discarding cover for use in an endoscope system including an endoscope having an insertion section to be inserted into a cavity under inspection and an operation section to which a proximal end of the insertion section is connected, and a disposable protection cover having an insertion section cover for covering the insertion section of the endoscope, includes an improvement being characterized in that said discarding cover has formed therein a cavity into which the insertion section cover is insertable and comprises a means for fixing a distal end portion of the insertion section cover at a distal end portion of the discarding cover.

In the discarding cover according to the invention, after the used insertion section of the endoscope has been inserted into the discarding cover, the distal end portion of the insertion section is secured to the discarding cover by operating the fixing means, so that the insertion section can be easily removed from the insertion section cover.

BRIEF DESCRIPTION OF THE DRAWINGS

FIG. 6 is a longitudinal cross sectional view depicting the construction of another embodiment of the endoscope system according to the invention;

FIG. 7 is a cross sectional view representing the detailed construction of the shaft of the operation section;

FIG. 8 is a cross sectional view showing the construction of the distal end of the embodiment shown in FIG. 7;

FIG. 9 is a schematic cross sectional view showing another embodiment of the endoscope system according to the inventions;

FIG. 10 is a schematic cross sectional view showing still another embodiment of the endoscope system according to the invention;

FIG. 11 is a perspective view representing an embodiment of the package for installing the protection cover set according to the invention;

FIG. 12 is a perspective view showing a packing box according to the invention;

FIG. 13 is a partially cross sectional view illustrating the side walls of the box shown in FIG. 12;

FIG. 14 is a plan view showing a label applied on the box shown in FIG. 12;

FIG. 16 is a perspective view illustrating still another embodiment of the protection cover set package according to the invention;

FIG. 17 is a perspective view showing the package in the expanded condition;

FIG. 18 is a perspective view representing the condition in which the endoscope is covered with the protection cover within the package;

FIG. 19 is a perspective view showing an embodiment of the outer tube according to the invention;

FIG. 20 is a cross sectional view illustrating the distal end of the outer tube shown in FIG. 19; and FIG. 21 is a cross sectional view showing another embodiment of the outer tube according to the invention.

EXPLANATION OF THE PREFERRED EMBODIMENTS

Figure 1:
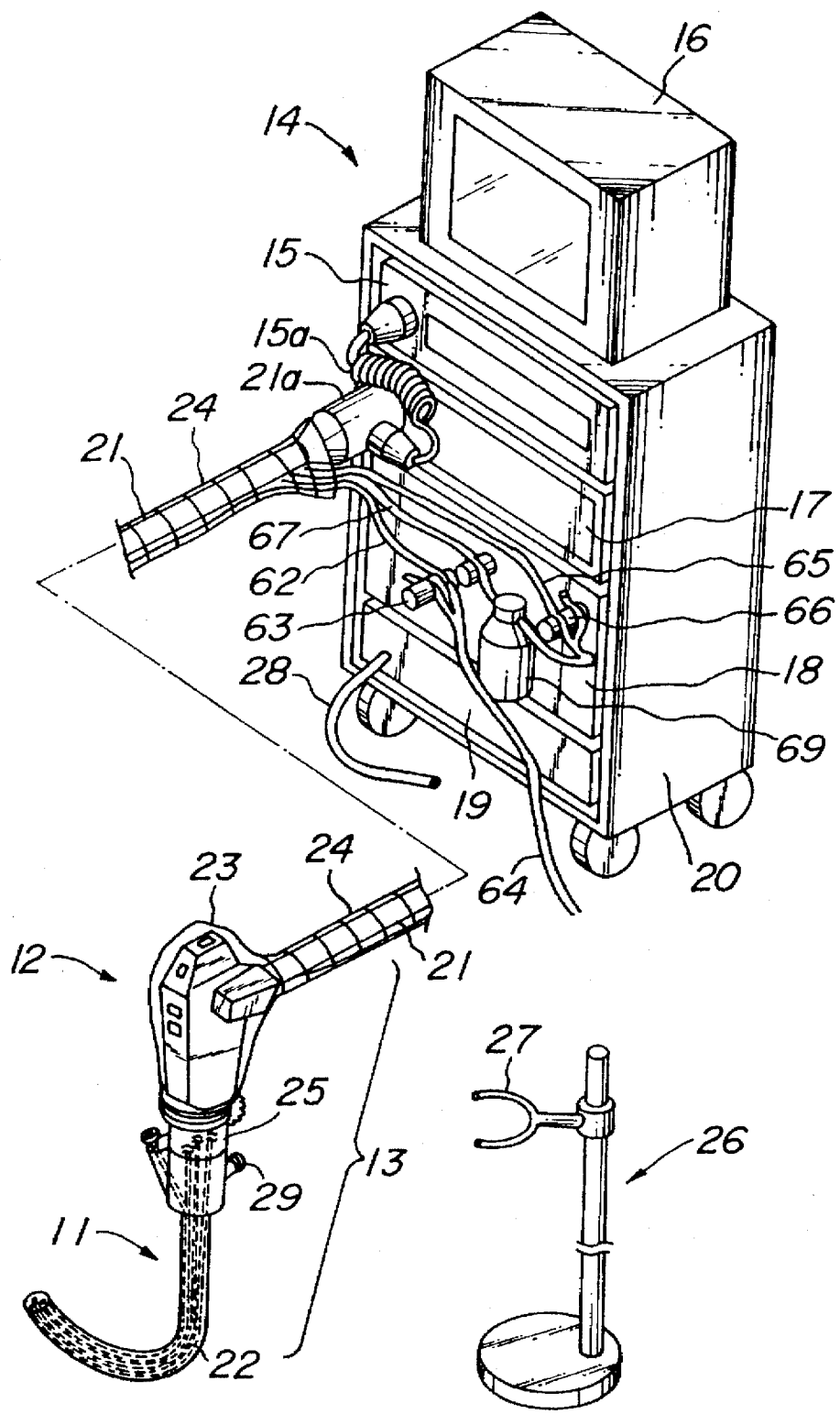
FIG. 1 is a perspective view showing the whole construction of an embodiment of the endoscope system according to the invention.

FIG. 1 is a schematic view showing an embodiment of the endoscope system according to the invention including an endoscope apparatus and disposable protection cover the endoscope apparatus comprises an endoscope 13 having an insertion section 11 and an operation section 12 with which a proximal end of the insertion section is coupled, and an external apparatus 14 coupled with the endoscope 13, the external apparatus 14 comprises a video processor 15 having a circuit for driving a solid state image sensor provided within a distal end of the insertion section 11 and a circuit for processing an image signal read out of the solid state image sensor, a monitor device 16 for displaying an image of an object under inspection by processing the image signal supplied from the video processor 15, a light source device 17 for emitting light for illuminating an inside of a cavity by means of a light guide optical fiber bundle extending within the insertion section 11, a fluid control device 18 having an air pump for supplying air and water, and an inflator 19 for inflating the disposable protection cover such that the insertion section 11 of the endoscope 13 can be easily inserted into and removed from the disposable protection cover as will be explained later in detail. These devices are installed in a box 20 having casters. The video processor 15 and light source device 17 are coupled with the operation section 12 of the endoscope 13 and the fluid control device 18 is coupled with conduit channels provided within the disposable protection cover by means of signal conducters, light guide optical fiber bundle and tubes, respectively. These signal conductors, light guide optical fiber bundle and tubes are combined with each other into a universal cord 21. The construction and operation of the above mentioned devices except for the inflator 19 are well known in the art, so that the detailed explanation thereof is dispensed with.

The disposable protection cover of the present embodiment comprises an insertion section cover 22 for covering the insertion section 11 of the endoscope 13, an operation section cover 23 for covering the operation section 12 of the endoscope and a universal cord cover 24 for covering the universal cord 21. These disposable protection covers 22, 23 and 24 are formed separately from each other, and suitable coupling mechanisms are provided between junctions thereof in order to avoid a possible contamination through the junctions.

The protection covers 22, 23 and 24 may be made of various materials. For instance, flexible vinyl and rubber may be used as a soft material and rigid or semi-rigid plastics may be used as a hard material. It should be noted that the protection covers 22, 23 and 24 are not always necessary to be made of the same material, but may be made of different materials. For instance, the insertion section cover 22 may be made of flexible rubber, the operation section cover 23 may be made of rigid plastics and the universal cord cover 24 may be made of semi-rigid vinyl.

Prior to the actual examination, a set of protection covers is removed from a package and a connecting portion 25 made of rigid or semi-rigid plastics and provide at a proximal end of the insertion section cover 22 is hung from a cover supporting member 27 of a cover supporting stand 26. In order to prevent the connecting portion 25 from being contaminated, the cover supporting member 27 may be covered with a disposable cover. As will be explained later, the connecting portion 25 of the insertion section cover 22 is utilized to couple the insertion section cover with the operation section cover 23.

A height of the cover supporting stand 26 has to be adjusted such that when the insertion section cover 22 is hung from the cover supporting member 27, the distal end of the disposable insertion section cover is not brought into contact with a floor. However, if a height of the cover supporting stand 26 is made too high, the inserting operation becomes difficult, so that the cover supporting stand could not be made so high. In such a case, the insertion section cover 22 has to be supported by an operator.

After the insertion section cover 22 has been hung from the cover supporting member 27, an end of an air supply tube 28 connected to the inflator 19 is coupled with a nipple portion 29 provided in the connecting portion 25 of the insertion section cover 22, and then the inflator 19 is derived to supply an air through the tube 28 into insertion section cover 22. In this manner, the insertion section cover 22 is inflated, so that the insertion section 11 of the endoscope 13 can be easily inserted into the insertion section cover 22. Then, the inflator 19 is de-energized and the tube 28 is decoupled from the nipple portion 29, this inflating operation is also performed upon removing the insertion section 11 form the insertion section cover 22. After the examination, the protection covers 22, 23 and 24 are discarded as medical dusts and the endoscope is cleaned and sterilized after all examinations for one day have been finished.

Figure 2:
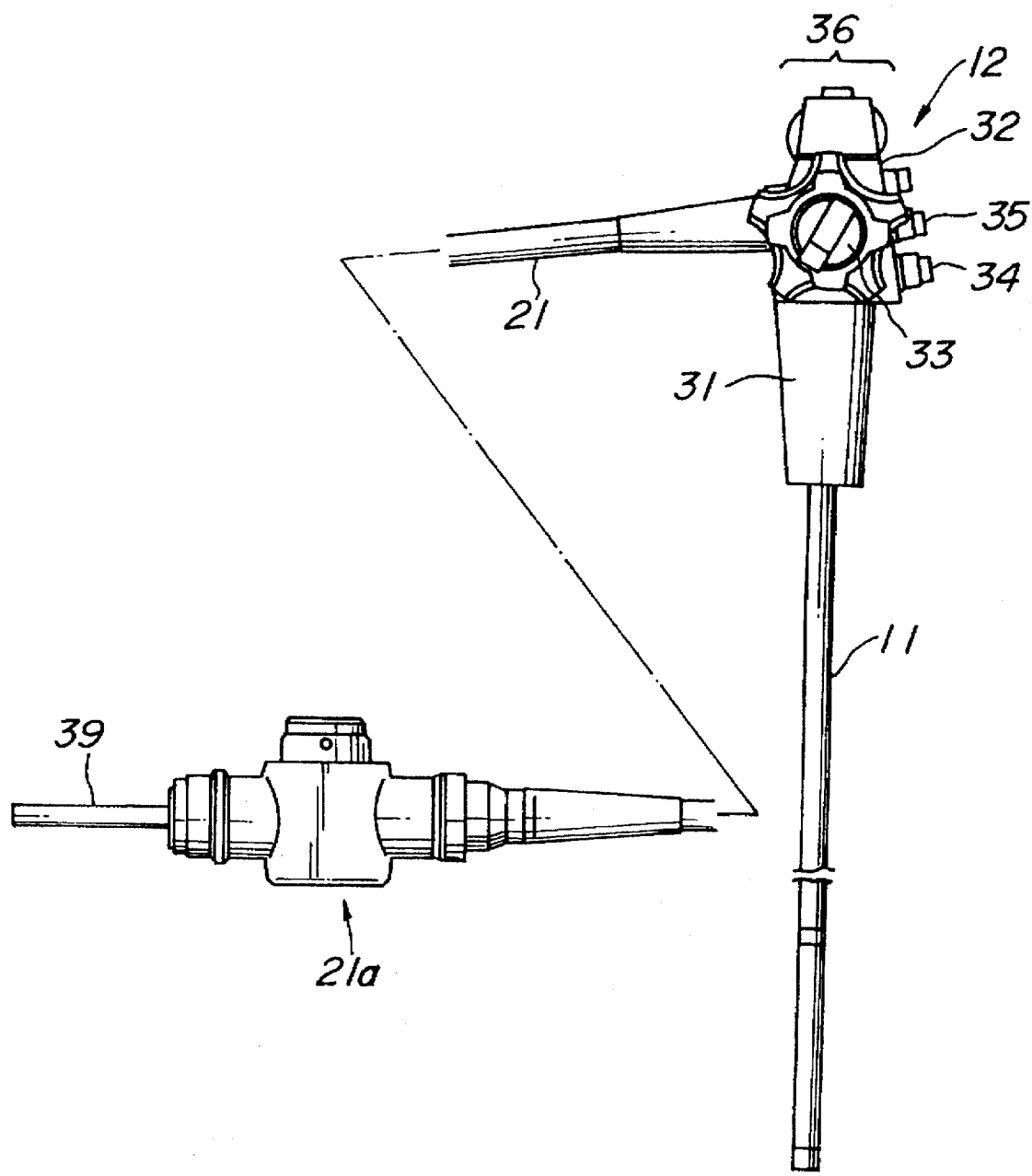
FIG. 2 is a front view illustrating the construction of the operation section of the endoscope shown in FIG. 1.

FIG. 2 shows the construction of the operation section 12 of the endoscope, to the operation section 12 are connected the insertion section 11 and universal cord 21, the operation section comprises a grip portion 31 and a main portion 32. The main portion 32 comprises angle knobs 33 for bending the distal end of the insertion section 11, air and water supply control switch 34, suction control switch 35 and function switch 36 for controlling the operation of a camera taking photographs of the object under inspection. In the present embodiment, the angle knobs 33 are detachably secured to the main portion 32 of the operation section 12. The angle knobs 33 may be of a disposable type which is contained in a package in which the disposable protection cover is installed or may be reused after sterilization.

Figure 3:
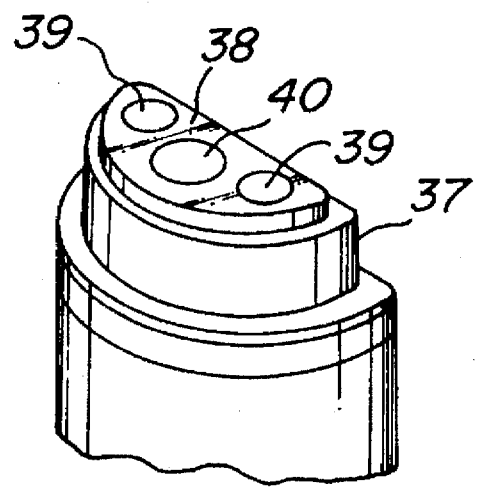
FIG. 3 is a perspective view depicting the distal end of the insertion section of the endoscope.

FIG. 3 is a perspective view illustrating the construction of the insertion section 11 of the endoscope. In the present embodiment, a lateral cross section of a distal end construction member 37 is semicircular and in a front surface 38 of the member 37 there are arranged outlets of a pair of illuminating optical systems, i.e. optical fiber bundles 39 and an aperture 40 of an observing optical system provided between the illuminating optical systems.

Figure 4:
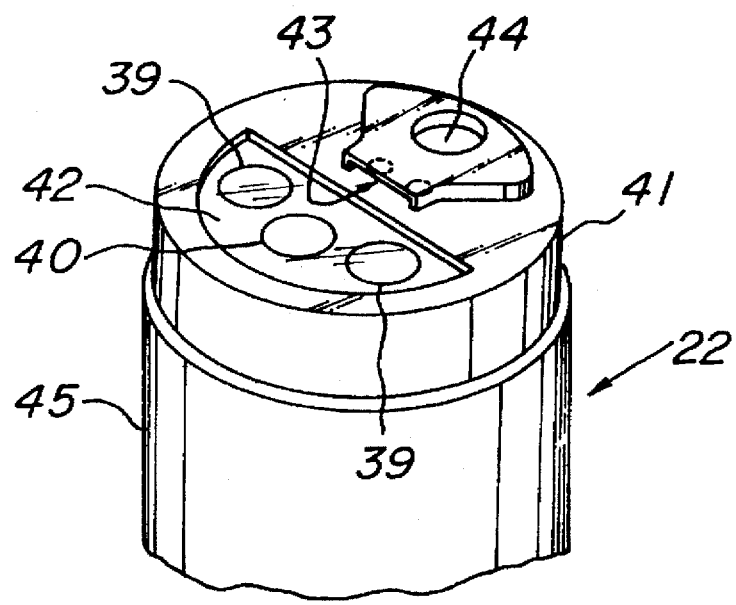
FIG. 4 is a perspective view illustrating the construction of the distal end of the insertion section cover.
Figure 5:
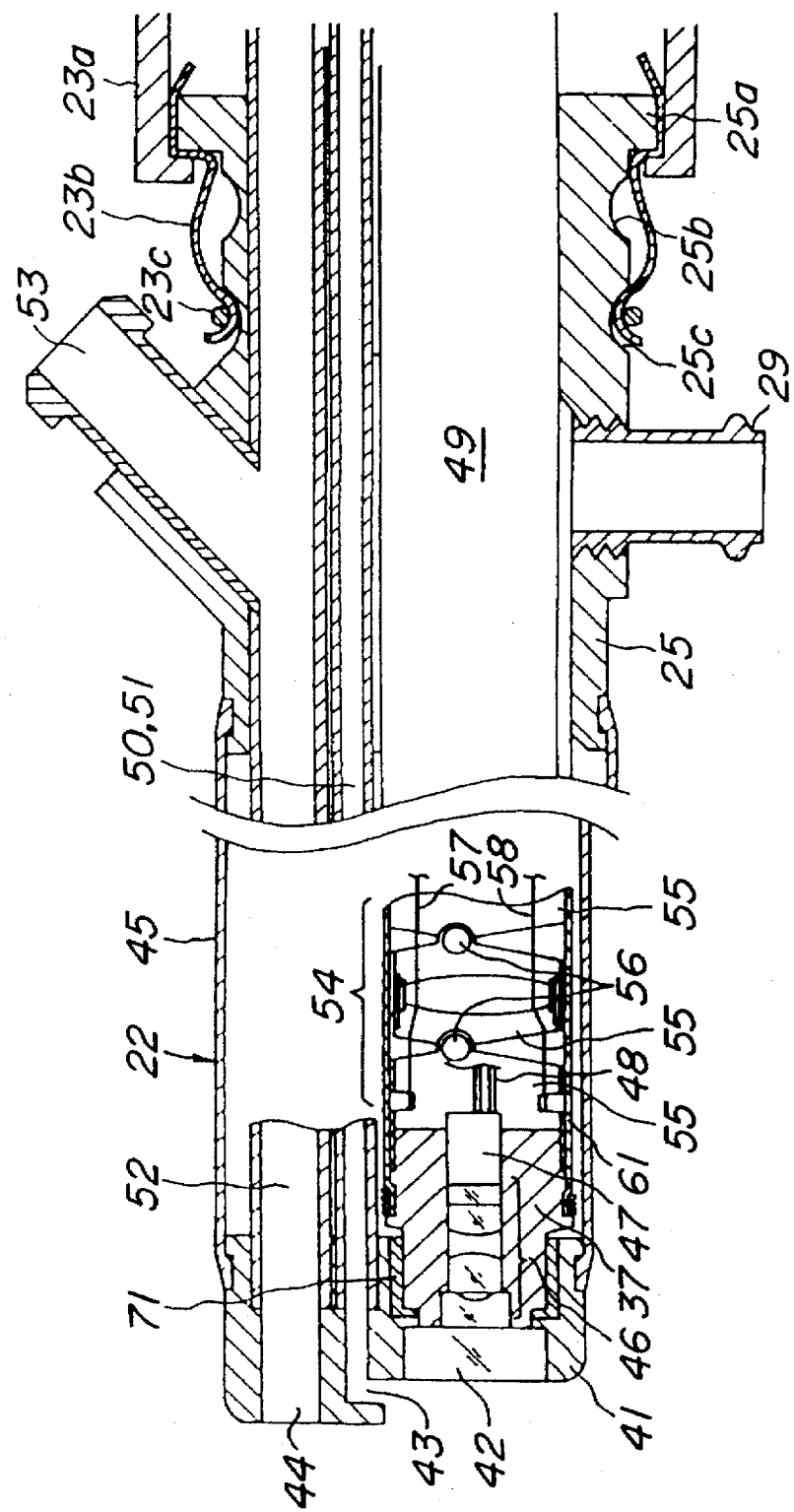
FIG. 5 is a longitudinal, cross sectional view showing the endoscope system shown in FIG. 1.

FIG. 4 is a perspective view depicting the construction of a distal end of the insertion section cover 22 and FIGS. 5 and 6 are longitudinal and lateral cross sectional views showing the insertion section cover 22 into which the insertion section 12 of the endoscope is inserted. In a front surface of a distal end construction member 41 of the insertion section cover 22, there are provided a semicircular observation window 42 made of transparent material, a nozzle 43 for ejecting air and water toward the window 42, and an outlet opening 44 of a forceps channel 52. By ejecting the air and water from the nozzle 43, the outer surface of the observation window 42 can be cleaned.

To the distal end construction member 41 of the insertion section cover 22, is connected one end of an insertion section cover tube 45 which isolates a main portion of the insertion section 12 from the external environment. This cover tube 45 is made of a flexible material. In the present embodiment the cover tube 45 is made of flexible rubber. The other end of the cover tube 45 is connected to the connecting portion 25 of the insertion section cover 22.

As illustrated in FIG. 5, within the distal end construction member 37 of the insertion section 11 which is faced with the observation window 42 of the distal end contraction member 41 of the insertion section cover 22, there are arranged observing lens system 46 for forming an image of an object under inspection and a solid state image sensor 47 for picking-up the image of an object under inspection. The solid state image sensor 47 is electrically connected to the video processor 15 (FIG. 1) by means of signal conductors 48 extending through the insertion section 11 and universal cord 15.

Within the insertion section sower 22, there are formed endoscope insertion channel 49 into which the insertion section 11 is inserted, air supply conduit 50 communicated with the air and water ejecting nozzle 43, water supply conduit 51 also communicated with the nozzle 43, and forceps channel 52. These channels and conduits are formed by interior walls and protection cover 22 and are arranged in parallel with each other as shown in FIG. 5. The forceps channel 52 is communicated with a forceps inlet opening 53 provided in the connecting portion 25 and is also communicated with the fluid control device 18 by means of a conduit tube provided within the universal cord 21. Therefore, the forceps channel 52 is used as a suction tube and is sometimes called a suction channel. Further, the conduits 50 and 51 are also called conduit channels in the present specification.

In order to bend the distal end of the insertion section 11 by operating the angle knobs 33 such that an optical axis of the observing optical system 46 is moved up and down as well as right and left, there is provided a bending portion 54 adjacent to the distal end construction member 37 of the insertion section 11 of the endoscope. The bending portion 54 comprises a series of nodal rings 55 which are coupled with each other by means of journal pins 56 and a front end ring is connected to the distal end construction member 37 of the insertion section 11. Two pairs of wires 57, 58 and 59, 60 are secured to the front end ring 55 at diametrically opposing points. These wires 57 to 60 are extended within the insertion section 11 and are wound around a pair of pulleys provided in the operation section 12, in FIG. 5, only one pair of wires 57 and 58 are shown, but two pairs of wires 57 to 60 are illustrated in FIG. 6. A series of nodal rings 55 is covered with a flexible rubber tube 61 in a liquid tight manner. By operating the angle knobs 33, the pulleys may be rotated and thus the wires 57 to 60 may be moved such that the bending portion 54 is moved in the up and down directions as well as in the left and right directions and the distal end of the insertion section 11 is directed into a desired direction. This construction is well known in the art, so that its detailed explanation may be dispensed with. At a proximal end of the connecting portion 25 there are formed a ring shaped recess 25a for connecting the operation section cover 23 and a ring shaped recesses 25b for engaging the connecting portion with the supporting member 27 on the supporting stand 26.

As illustrated in FIG. 1, the suction channel 52 is communicated with a first suction tube 62 which is connected via a section control valve 63 to a second suction tube 64 which is further communicated with a suction pump not shown in FIG. 1. The air supply conduit channel 50 is communicated with an air supply tube 65 by means of an air supply control valve 66 and the water supply conduit channel 51 is communicated with a water supply tube 67 which is connected via a water supply control valve 68 to a water tank 69. The air and water supply pump is arranged in the fluid control device 18.

In the present embodiment the air and water supply conduit channels 50 and 51 and the forceps channel 52 are formed in the form of a multi-lumen tube 70 as shown in FIG. 6. The multi-lumen tube 70 has a semi-circular cross section and is provided in an upper half portion of the cover tube 45. In the remaining semi-circular lower half portion of the cover tube, there is inserted the insertion section 11 of the endoscope 13 such that the bending portion of the insertion section can be correctly bent in a direction in which the insertion section and multi-lumen tube 70 are arranged side by side. According to the invention, this direction is aligned in the up and down directions. Therefore, the bending portion of the insertion section 11 can be precisely bent in the up and down directions without being influenced by the multi-lumen tube 70. That is to say, the multi-lumen tube 70 is arranged such that the forceps channel 52 is shunted in the diametric direction in which the insertion section 11 and multi-lumen tube 70 are arranged and the air and water supply channels 50 and 51 are symmetrical situated with respect to the diametric direction. Therefore, the distal end of the insertion section 11 can be bent correctly in the up and down directions by operating the angle knob 33. In FIG. 6, the light guide optical fiber bundle and signal conductors connected to the solid state image sensor are not shown for the sake of simplicity. Further, it should be noted that the multi-lumen tube 70 may be formed integrally with the cover tube 45.

In the present embodiment, as depicted in FIG. 5, at a distal end of the insertion section inserting channel 49 of the insertion section cover 22 there is provided a tube-like contact member 71 made of resilient material into which the distal end of the insertion section 11 of the endoscope. Therefore, when the insertion section 11 of the endoscope is inserted into the insertion section inserting channel 49 formed in the insertion section cover 22, the distal end of the insertion section is brought into contact with the contact member 71 and the distal end of the insertion section can be effectively protected from the damage. An inner diameter of the insertion section inserting channel 49 is larger than an outer diameter of the insertion section 11 except for the distal end portion, so that the insertion section can be easily inserted into and removed from the inserting channel 49. At the same time, the distal end of the insertion section 11 of the endoscope is fixed in position by means of the contact member 71, and thus any shift in the relative position of the insertion section 11 with respect to the insertion section cover 22 can be avoided effectively. Further the bending portion 54 of the insertion section is provided near the distal end portion, the distal end portion is firmly secured to the insertion section cover 22 by means of the contact member 71, and therefore the distal end can be correctly directed to any desired direction by operating the angle knobs 33.

FIG. 7 is a cross sectional view showing another embodiment of the endoscope system affording to the invention. In the present embodiment, portions similar to those of the previous embodiment are denoted by the same reference numerals used in FIG. 6. In the present embodiment, the multi-lumen tube 70 is formed to have a cross section of a segment having a center angle smaller than 180 degrees and the insertion section 11 is inserted into the remaining space. Also in the present embodiment, the insertion section 11 and multi-lumen tube 70 are aligned in the up and down directions. That is to say, the downward moving wire 58 is closest to the multi-lumen tube 70. Therefore, the distal end portion of the insertion section 11 can be bent correctly in the up and down directions. Further, in the present embodiment, the insertion section 11 has a larger cross sectional area, and therefore the light guide optical fibers 39 can has a large diameter and a bright image of the object can be monitored. According to the invention, the multi-lumen tube 70 may have a larger cross sectional area than the insertion section 11. Then, the air and water supply channels 50 and 51 and the suction channel 52 may be formed to have large diameters and the air and water supply and suction can be performed effectively.

In the present embodiment, as shown in FIG. 8, the distal end construction member 37 of the insertion section 11 is inserted into the contact member 71 made of resilient material, and further the bending portion 54 of the insertion section 11 is inserted into a small diameter portion 49a of the insertion section inserting channel 49 formed within the sorer tube 45. A remaining portion 49b of the insertion section inserting channel 49 has a larger diameter than that of the insertion section 11. In the present embodiment, the inner diameter of a substantial part of the insertion section inserting channel 49 is larger than the outer diameter of the insertion section 11, and thus when the insertion section inserting channel 49 is inflated, the insertion section can be easily inserted into and removed from the insertion section inserting channel. As the case may be, it may not be necessary to inflate the insertion section inserting channel 49.

Further, the whole body of the bending portion 54 of the insertion section 11 is firmly inserted into the small diameter portion 49a, so that the distal end of the insertion section 11 can be moved correctly in the up and down directions by operating the wires 57 and 58. In this uses, the distal end of the insertion section 11 is hardly deflected in the right or left direction, because the multi-lumen tube 70 and insertion section 11 of the endoscope are arranged in the up and directions. In the present embodiment, the multi-lumen tube 70 is arranged below the insertion section 11 and the upwardly bending wire 57 is remote from the multi-lumen tube 70, the upward movement can be performed particularly easily and precisely.

In the embodiments explained above, the conduit channels 50 to 52 are formed within the multi-lumen tube 70, but these conduit channels may be formed by independent tubes as shown in FIG. 9 or a single conduit channel 75 as illustrated in FIG. 10. In FIGS. 9 and 10, the insertion section 11 is denoted as a solid body for the sake of simplicity. Moreover, in the above embodiments, the insertion section of the endoscope has a semicircular cross section, but the insertion section may be formed to have a circular cross section. Even in this case, the insertion section and conduit channel or channels are aligned in the up and down directions.

FIG. 11 is a perspective view showing a set of the disposable protection cover installed in a package. That is to say, this set of the disposable protection cover comprises cover supporting member cover 161 for covering the cover supporting member 26 of the cover supporting stand 25 shown in FIG. 1, insertion section cover 22, operation section cover 23, angle knob assembly 33 detachably secured to a shaft provided on the operation section 12 and universal cord cover 24, and these parts are installed within respective packages 164a to 164e These packages 164a to 164e are stacked one on the other in this order and an assembly of the packages is covered with a clean vinyl resin sheet and is installed within a packing box 170 made of corrugated cardboard as depicted in FIG. 12.

Within the package 164b, the insertion section cover 23 is inserted into a disposable mouth piece 180. The cover supporting member cover 161 includes an open end 165 in which a rubber band is provided and two bifurcated ends 166 and 167. The operation section cover 23 is formed by a tube-like member made of vinyl resin sheet and having open ends at which rubber bands are provided. The angle knob assembly 163 comprises right/left angle knob 168 and up/down angle knob 169 which are coupled with each other coaxially. When the operation section cover 23 is applied on the operation section 12 of the endoscope, the shaft is projected from the cover and the angle knob assembly 163 is detachably secured to the shaft. After the examination, the angle knob assembly 163 is removed from the shaft. In the present embodiment, the universal cord cover 24 is formed by a tube-like member having open ends at which rubber bands are secured and a fastener 24a extending from one end to the other end is provided Within the package 164c, there is arranged a portion 176 for detecting or indicating an opened condition of the package. That is to say, anhydrous $CuSO_4$ powder is applied on the portion 176. When the package 164c is opened and a moisture is introduced into the package, color of the portion 176 is changed into blue by a reaction $CuSO_4 + 4H_2O \rightarrow CuSO_4 \pm H_2O$. In this manner, a user can know a time period which has been elapsed after the package was opened.

As shown in FIG. 12, the packing box 170 comprises a lid 171 which is hinged along one side of the box on both sides of the box 170 there are provided connecting portions 172 and 173. As illustrated in FIG. 13, more than two boxes 170 may be coupled with each other by engaging the connecting portions 172 and 173. On a front side wall of the box 170, a label 175 depicted in FIG. 14 is applied. On the label 175 there are described a data on which the sterilizing was performed and a time limit of effective term.

Now a manner of using the disposable protection cover will be explained. At first, a desired endoscope is taken out of a scope stocker and then the endoscope is coupled with the external apparatus 14 shown in FIG. 1. Then, the power switch of the external apparatus 14 is made on and the inflator switch is also made on. During this operation, the endoscope is held on a suitable scope hanger not shown.

Next the packing box 170 in which the protection cover matched with the selected endoscope is taken out and is opened. At first, the uppermost package 164a is opened and cover supporting member cover 161 is taken out and then this cover is applied onto the cover supporting member 26 of the cover supporting stand 25 (see FIG. 1). Then, the second package 164b is opened to take out the insertion section cover 22 with the mouth piece 180, and the insertion section cover is hung from the cover supporting member 26. Next the inflating tube 28 shown in FIG. 1 is connected to the nipple portion 29 to inflate the insertion section inserting channel 49, and then the insertion section 11 of the endoscope is inserted into the insertion section inserting channel such that the distal end of the insertion section 11 is firmly inserted into the contact member 71 provided at the distal end of the insertion section cover,22. At the same time the lower end of the operation section 12 of the endoscope is inserted into the connecting portion 25. After that, the inflating tube 28 is removed from the nipple portion 29 and tubes coupled with the conduit channels formed within the insertion section cover 23 are connected to the fluid control device 18.

Next, the third package 164c is opened to take out the operation section cover 23 and then the operation section 12 of the endoscope is covered with the operation section cover 23, while the shaft is protruded out of the operation section cover. After the fourth package 164d is opened and the angle knob assembly 163 is taken out, the angle knob assembly is detachably secured to the shaft. Finally the last package 164e is opened to take out the universal cord cover 24 and the universal cord 21 is covered with the cover 34.

As explained above, in the present embodiment, all parts of the set of the protection cover set including the cover supporting member cover 161 and angle knob assembly 163 are packed as a single unit, the preparation for the examination can be carried out simply and positively. Further, the packages 164a to 164e are stacked one on another, the preparing operation can be performed without error by successively opening these packages from the uppermost one.

Moreover, a plurality of packing boxes 170 are coupled with each other by means of the connecting members 172 and 173, they can be easily transported. Further, the label 175 bearing the sterilizing date and effective date is applied on the box 170, the user can easily reject a box whose effective date has passed, and thus the contamination can be further positively prevented. Furthermore, the portion 176 for indicating the time elapsing from a time at which the package was opened is provided, and therefore a box which might be contaminated during a long time period after the box was opened can be prevented from being used.

According to the invention, the labels bearing the sterilizing date and/or effective date may be applied on all the packages 164a to 164e. In this case, the packages 164a to 164e may be discarded after opening. Further the opening indicating portion 176 may be provided on the operation section cover 23. A plurality of packing boxes 170, e.g. ten boxes may be packed as a unit pack.

Figure 15:
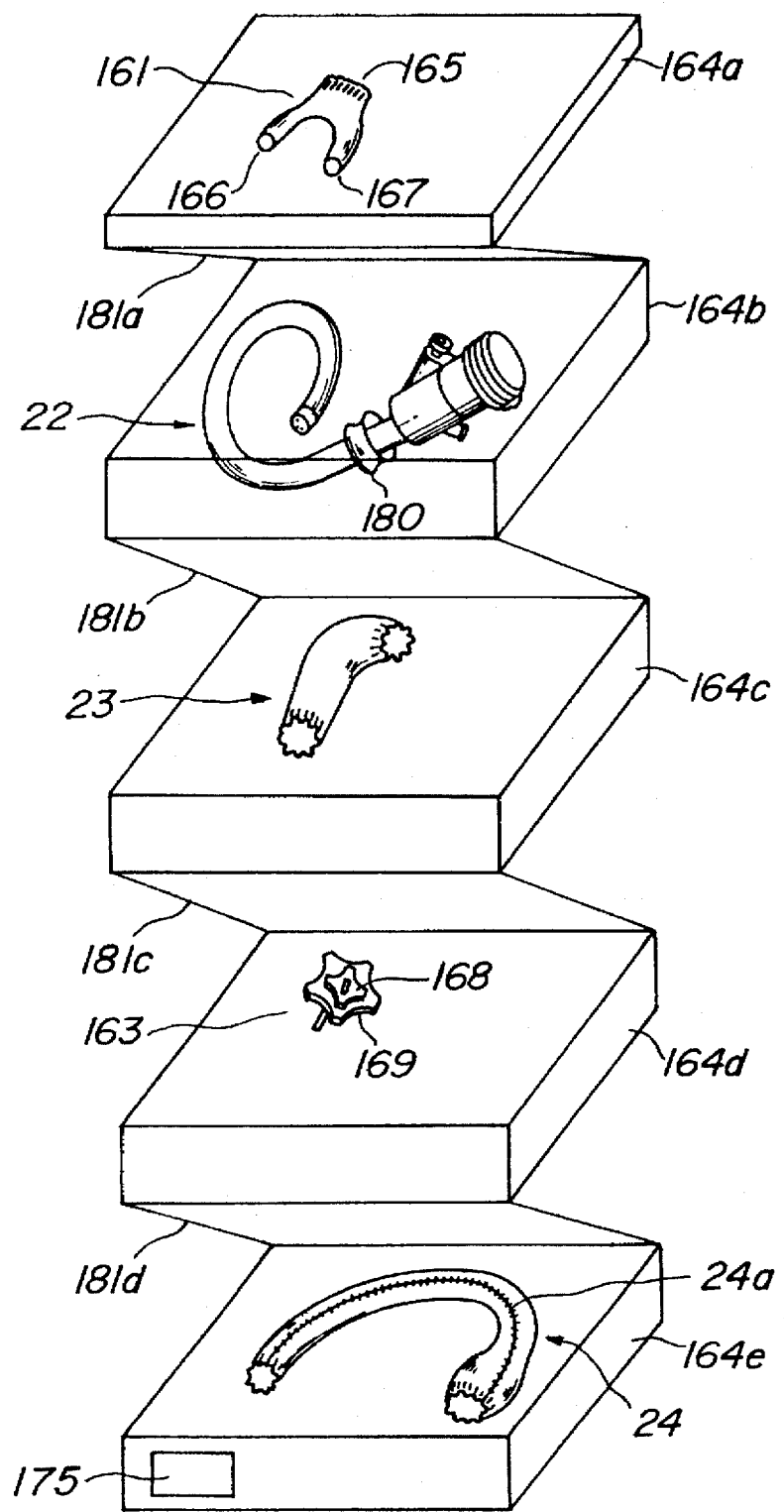
FIG. 15 is a perspective view showing another embodiment of the protection cover set package according to the invention.

FIG. 15 is a perspective view showing another embodiment of the package for packing the protection cover set according to the invention. In the present embodiment, portions similar to those illustrated in FIG. 11 are denoted by the same reference numerals in FIG. 11. In the present embodiment, packages 164a to 164e are made of light shielding material and adjacent packages are connected with each other by means of connecting members 181a to 181d such that these packages are folded. On parts of the cover supporting member cover 161, insertion section cover 22, operation section cover 23, angle knob assembly 163 and universal cord cover 24 are provided photosensitive portions. Once a package is opened, a photosensitive portion is exposed to light and its color is changed. Further a label 175 bearing sterilizing date and effective date is applied on the package 164e. The remaining construction of the present embodiment is entirely same as the previous embodiment.

Also in the present embodiment, the endoscope can be covered with the protection cover in an easy and accurate manner, while the parts of the protection cover set are hardly disappeared, because all the packages 164a to 164e are connected with each other. Further the protection cover set which might be contaminated after the packages have been opened can be effectively prevented from being used.

FIGS. 16 to 18 show another embodiment of the package for the protection cover according to the invention. Also in the present embodiment portions similar to those of the previous embodiments are represented by the same reference numerals used in the previous embodiments. Within a packing box 170, a package 164 is installed as being folded. On a front wall of the box 170 is applied a label 175 denoting the sterilizing date and/or effective date. On one side wall 100 of the box 170 a permanent magnet is secured and the opposite side wall 101 is made of magnetic material such as iron.

In the present embodiment, the package 164 is formed in the form of a tube-like bag and is made of easily deformable transparent plastics, upper and lower ends of the tube-like package being closed. Within the package 164, there are provided all the necessary parts of the protection cover set such as the insertion section cover 22, operation section cover 23, universal cord cover 24, angle knob assembly 163, mouth piece 180 and so on. On a rear surface of a top portion of the package 164 is secured one end of a hanging cord 102 and the connecting portion 25 of the insertion section cover 22 is secured to the lower end of the funding cord such that the connection therebetween can not be separated by a relatively strong force. The hanging cord 102 comprises branches 102a and 102b to which the angle knob assembly 163 and universal cord cover 24 are respectively secured in such a manner that these parts can be separated from the branches only by pulling them with strong force.

On the outer surface of the top portion of the package 164 is secured a hanging band 103 by means of which the package is hung from a hook 105 of a hanger 104 as shown in FIG. 17. In this condition, the connecting portion 25 of the insertion section cover 22 situates above the floor. When the package 164 is hung from the hanger 104, the user can clearly see the all the parts of the protection cover set through the transparent package. According to the invention, these parts are provided within the package 164 in such a manner that the user can easily know the order in which these parts are successively used.

As shown in FIG. 17, to the connecting portion 25 is connected one end of an inflating pipe 109 and the other end of this pipe is protruded from the package 164 in an airtight manner and is provided with a nipple portion 29. At a middle portion of the package 164 there are formed openings 106, 107 and 108 such that these openings are communicated with the outside of the package. The opening 106 is communicated with the insertion section inserting channel 52 formed within the insertion section cover 22, and the ends of the openings 107 and 108 are formed as gloves. It should be noted that these openings 106 to 108 are not communicated with the inside of the package 164, so that the cover parts such as the insertion section cover 22, operation section cover 23, universal cord cover 24, angle knob assembly 163 and mouth piece 180 are prevented from being contaminated.

Now the preparatory operation for covering the endoscope with the protection cover will be explained. The package 164 is taken out of the box 101 end is hung from the hanger 104 as shown in FIG. 17. Then, the inflating tube 28 illustrated in FIG. 1 is secured to the nipple portion 29 to inflate the insertion section inserting channel of the insertion section cover 22. Then, the insertion section of the endoscope is inserted into the insertion section inserting channel via the opening 106 such that the lower portion of the operation section of the endoscope is firmly inserted into the connecting portion 25. During this operation, the user inserts both hands into the openings 107 and 108 and can grasp the protection cover parts without contaminating them. After that, the inflating tube 28 is disconnected from the nipple portion 29.

Next, the operation section cover 23 is separated from the package 164 at the opening 106 and its open end is closed by a rubber band. Then, the angle knob assembly 163 is separated from the branch 102a and is secured to the shaft provided on the operation section of the endoscope and protruded from the operation section cover 23. After the conduit tubes extending from the connecting portion 25 have been connected to the fluid control device 18 shown in FIG. 1, the universal cord cover 24 is separated from the branch 102b and the universal cord and conduit tubes are covered with the universal cord cover by utilizing the fastener 24a. FIG. 18 shows the condition in which the above mentioned operation has been done. Then, the connecting portion 25 of the insertion section cover 22 is separated from the hanging cord 102, and the endoscope having the protection cover applied thereon is removed from the package 164 via the opening 106. After the examination, the endoscope with the protection cover is inserted into the package and the protection cover is removed from the endoscope. The used protection cover as well as the angle knob assembly and mouth piece may be discarded together with the package 164.

In this manner, by using the package 164 of the present embodiment, the protection cover can be kept clean within the package not only prior to the usage but also during the operation for covering the endoscope with the cover. Further, the user's hands can be inserted into the package through the openings 107 and 108, the operation can be performed easily and positively. Moreover, the necessary parts of the protection cover including the angle knob assembly and mouth piece are installed within the package such that the order of using these parts can be easily understood by the user. After the examination, the used protection cover can be removed from the endoscope within the package and the thus removed protection cover can be discarded together with the package. Therefore, the surrounding can be effectively prevented from being contaminated.

Further, in the present embodiment, the permanent magnet and magnetic plate are provided on opposite side walls of the box 170, so that a plurality of boxes can be coupled with each other and the transportation and stock of the boxes can be performed positively.

In a modification of the above explained embodiment, serial numbers are applied on the parts of the protection cover set in accordance with an order in which these parts are successively used. For instance, "1" is applied on the connecting portion 25, "2" is applied on the insertion section cover 22, "3" is applied on the angle knob assembly 163, "4" is applied on the universal cord cover 24 and so on. Then, these parts can be used in a correct order.

FIGS. 19 and 20 are perspective and cross sectional views showing an embodiment of the outer tube according to the invention. The outer tube is utilized as a tool for removing the used insertion section of the endoscope from the insertion section cover after the examination. That is to say, after the examination, the assembly of the insertion section of the endoscope and the insertion section cover is removed from a cavity of a patient and then is inserted into the outer tube as illustrated in FIG. 19.

An outer tube 250 comprises a rubber tube 252 having a small thickness, a distal end portion 253 made of rigid material, and a proximal end portion 254 made of rigid material. The distal end portion 253 comprises a tube receptacle member 255, a clamping member 256 made of resilient material, and a fixing member 257. To the tube receptacle member 255, is secured one end of the rubber tube 252. As shown in FIG. 20, the tube receptacle member 255 has formed therein a male screw portion 258a and a holding portion 258b for supporting the resilient clamping member 256. The fixing member 257 is formed in a form of a tube and has formed therein a female screw portion 259 which is engaged with the male screw portion 258a. The rubber tube 252 has such a length that in the non-expanded condition, the nipple portion 29 provided on the connecting portion 25 is exposed, but in the expanded condition the connecting portion 25 is covered with the rubber tube 252. Further, instead of the resilient ring-shaped clamping member 256, use may be made of O-ring.

Now a manner of using the present outer tube will be explained. After the examination, water and air are sucked from the outlet opening 44 of the forceps channel 52 and the outer surface of the insertion section cover 22 is cleaned with an alcohol gauze. Then the universal cord cover 24 is removed and is discarded in a dust box. After that, the conduit tubes extending from the connecting portion 25 are disconnected from the fluid control device 18.

Next, the insertion section cover 22 is inserted into the cavity 251 of the outer tube 250 such that the distal end construction member 41 of the insertion section cover 22 is inserted into the ring-shaped clamping member 256 as illustrated in FIG. 20. Then, the fixing member 257 is rotated in a given direction such that the clamping member 256 is pushed by the fixing member toward the rubber tube 252 to deform the resilient clamping member 256. In this manner, the distal end contraction member 41 of the insertion section cover 22 is clamped in position by means of the deformed clamping member as depicted by a broken line in FIG. 20.

Then, the inflating tube 28 shown in FIG. 1 is connected to the nipple portion 29 to inflate the insertion section inserting channel 49 shown in FIG. 5, and the insertion section 11 of the endoscope is pulled out of the insertion section cover 22. In this case, the distal end of the insertion section cover 22 is clamped by the clamping member 256, so that the insertion section of the endoscope can be easily removed from the insertion section cover 22. After that, the inflating tube 28 is disconnected from the nipple portion 29 and the rubber tube 252 is expanded such that the connecting portion 25 of the insertion section cover 22 is covered with the rubber tube. Then, the proximal end portion 254 is rotated to close the rubber tube 252. This may be effected by using a rubber band. Finally the insertion section cover 22 is discarded together with the outer tube 250.

In the above embodiment, use is made of the rubber tube, but according to the invention, an expandable vinyl resin tube may be used. Moreover, in the above embodiment, the length of the rubber tube 252 is made longer than the length of the insertion section cover so that the insertion section cover can be inserted into the rubber tube. According to the invention, it is also possible to use a rubber tube having a large diameter and the insertion section cover may be inserted therein after being folded. In the above embodiment, the outer surface of the insertion section cover is cleaned with the alcohol gauze, but this may be dispensed with.

As explained above, when the outer tube explained above is used to discard the used insertion section cover, the insertion section of the endoscope can be removed from the insertion section cover without contaminating the hands of user. During this operation, the distal end of the insertion section cover is clamped in position within the outer tube, the insertion section of the endoscope can be easily removed from the insertion section cover.

FIG. 21 is a cross sectional view showing another embodiment of the outer tube according to the invention. In the present embodiment, the distal end construction member 41 is made of magnetic material and a permanent magnet 260 is fixed to the inner wall of the distal end portion 253 of the outer tube 250. When the insertion section cover 22 is inserted into the cavity 251 of the outer tube 250 such that the distal end of the insertion section cover 22 is close to the permanent magnet 260, the distal end contraction member 41 of the insertion section cover 22 is attracted to the permanent magnet. In this manner, the the distal end of the insertion section cover 22 is kept in position within the outer tube 250, so that the insertion section 11 of the endoscope can be easily removed from the insertion section cover 22.

In the endoscope system including the endoscope and protection cover, there are prepared a plurality of endoscopes having insertion sections of different diameters in accordance with optically properties. Then it is necessary to prepare plural kinds of protection covers having insertion section covers in which insertion section inserting channels having different inner diameters are formed. Then, there is a concern that a protection cover which is not matched with a given endoscope might be used. For instance, a protection cover with an insertion section inserting channel having a diameter smaller than an outer diameter of the insertion section of the endoscope is erroneously used, the insertion section cover might be broken and a contamination can not be avoided effectively. When a protection cover with an insertion section inserting channel having a diameter larger than an outer diameter of the insertion section of the endoscope is erroneously selected, the aperture 40 of the objective lens system 46 and light guide optical fiber bundles 39 might not be correctly positioned with respect to the window 42 of the insertion section cover 22, and thus the direction of the field of view might be deflected from a desired direction, the brightness of the image might be decreased and the image might be distorted. In order to avoid such drawbacks, according to the invention, the size of the aperture 40 of the objective lens system 46 and light guide optical fiber bundles 39 may be increased and the insertion section cover tube 45 may be expansible in the radial direction such that a plurality of insertion sections having different outer diameters can be inserted into a common insertion section cover.

Further, the rubber tube 252 of the outer tube 250 may have such a length that it can cover only the insertion section cover 22, moreover, the proximal end portion 254 of the outer tube 250 may be dispensed with.

What is claimed is:

1. An endoscope system comprising:
   an endoscope having an insertion section to be inserted into a cavity under inspection, the insertion section having a flat outer surface portion and a bending portion provided near a distal end thereof, said bending portion being bendable at least up and down with respect to a predetermined up/down movement axis, and an operation section to which a proximal end of the insertion section is connected; and
   a protection cover having an insertion section cover for covering the insertion section of the endoscope and having formed therein an insertion section inserting channel for receiving the insertion section of the endoscope therein and at least one conduit channel, said insertion section inserting channel and said at least one conduit channel being (i) defined by interior walls of said protection cover which separate the insertion section inserting channel and said at least one conduit channel from one another and include a flat portion for contacting said flat outer surface portion of the insertion section of the endoscope and (ii) arranged such that a line containing said up/down movement axis passes through both said flat portion of said insertion section inserting channel perpendicularly and said at least one conduit channel.

2. An endoscope system according to claim 1, wherein said at least one conduit channel is arranged downward of the insertion section inserting channel with respect to said up/down movement axis, so that the distal end portion of the insertion section of the endoscope can be bent in the upward direction without being affected by the at least one conduit channel.

3. An endoscope system according to claim 1, wherein a plurality of conduit channels are formed in the insertion section cover such that said plurality of conduit channels are arranged symmetrically with respect to said movement axis.

4. An endoscope system according to claim 3, wherein said plurality of conduit channels are formed as a multi-lumen tube.

5. An endoscope system according to claim 1, wherein the insertion section cover has formed therein second and third conduit channels, said at least one conduit channel and said second and third conduit channels being oriented substantially parallel to a longitudinal axis of the insertion section when the insertion section cover covers the insertion section and said second and third conduit channels being located respectively on opposite sides of a plane containing said up/down movement axis and said longitudinal axis of said insertion section.

6. An endoscope system comprising:

an endoscope having an insertion section to be inserted into a cavity under inspection, the insertion section having a bending portion provided near a distal end thereof which is bendable in at least up and down directions, and an operation section to which a proximal end of the insertion section is connected, and a protection cover having an insertion section cover for covering the insertion section of the endoscope, a distal end portion of the insertion section cover including means for clamping a distal end portion of the insertion section and said bending portion of the endoscope into the distal end portion of the insertion section cover and said protection cover including means for positioning the insertion section relative to said protection cover such that a remaining portion of the insertion section is substantially separated from interior walls of said insertion section cover, wherein said means for clamping comprises a contact member arranged within the distal end portion of the insertion section cover, said contact member being a cylindrical member having a hollow interior region and comprising resilient material and being shaped such that the distal end of the insertion section of the endoscope is firmly insertable into said hollow interior region of the contact member, and wherein said means for positioning comprises a small diameter portion and a large diameter portion formed by said interior walls of said insertion section cover, an inner diameter of said large diameter portion of the insertion section cover being larger than an outer diameter of said remaining portion of the insertion section, said large diameter portion of the insertion section cover and said remaining portion of said insertion section being disposed adjacent to one another at a location between the proximal ends thereof and the bending portion of the insertion section such that a space exists between said large diameter portion of the insertion cover and said remaining portion of said insertion section.

7. An endoscope system as in claim 6, wherein said small diameter portion of said protection cover contacts a portion of the insertion section between the distal end portion of the insertion section and said remaining portion of the insertion section.

8. A protection cover for use with an endoscope, said protection cover comprising:

an insertion section cover for receiving an insertion section of an endoscope therein, said endoscope having an insertion section including a bending portion near a distal end thereof and an operation section to which a proximal end of the insertion section is connected, the insertion section cover having a distal end portion including means for clamping a distal end portion of the insertion section of the endoscope and the bending portion of the endoscope into the distal end portion of the insertion section cover and the insertion section cover including means for positioning the insertion section of the endoscope relative to said insertion section cover such that a remaining portion of the insertion section is substantially separated from interior walls of the insertion section cover, wherein said means for positioning comprises (a) a first portion of said insertion section cover, said first portion contacting a portion of said insertion section between the distal end portion of the insertion section and said remaining portion of the insertion section, and (b) a second portion of said insertion section cover, an inner diameter of said second portion being larger than an inner diameter of said first portion, and said inner diameter of said second portion being larger than an outer diameter of said remaining portion of said insertion section, said second portion of the insertion section cover and said remaining portion of the insertion section being disposed adjacent to one another such that a space exists therebetween.

9. An endoscope system comprising:

an endoscope having an insertion section to be inserted into a cavity under inspection, the insertion section having a flat outer surface portion and a bending portion provided near a distal end thereof, said bending portion being bendable at least up and down with respect to a predetermined up/down movement axis, and an operation section to which a proximal end of the insertion section is connected; and a protection cover having an insertion section cover for covering the insertion section of the endoscope and having formed therein an insertion section inserting channel for receiving the insertion section of the endoscope therein and a plurality of conduits, said insertion section inserting channel and said plurality of conduits being (i) defined by interior walls of said protection cover which separate the insertion section inserting channel and said plurality of conduits from one another and (ii) arranged such that a line containing said up/down movement axis passes through the insertion section inserting channel and a conduit which has a largest diameter among said plurality of conduits, wherein said insertion section of the endoscope comprises a flat outer surface portion near the distal end thereof, said interior walls of the protection cover comprise a flat portion for contacting said flat outer surface portion of the insertion section of the endoscope, and said insertion section inserting channel and said plurality of conduits are arranged such that said line containing said up/down movement axis passes through said flat portion of the interior walls perpendicularly.

* * * * *